United States Patent [19]

Foster

[11] 3,999,067
[45] Dec. 21, 1976

[54] HIGH SPEED RADIATION SCANNING TECHNIQUE FOR SIMULTANEOUSLY DETERMINING THE PITCH AND ECCENTRICITY OF AN ENCASED OIL

[75] Inventor: Billy E. Foster, Oak Ridge, Tenn.

[73] Assignee: The United States of America as represented by the United States Energy Research and Development Administration, Washington, D.C.

[22] Filed: Oct. 14, 1975

[21] Appl. No.: 621,892

[52] U.S. Cl. ............................... 250/312; 250/359
[51] Int. Cl.$^2$ ................... G03C 9/00; G01M 23/00
[58] Field of Search .......... 250/312, 320, 321, 322, 250/333, 359

[56] References Cited

UNITED STATES PATENTS

| 2,465,676 | 3/1949 | De Ment | 250/321 |
| 2,511,853 | 6/1950 | Kaiser | 250/323 |
| 3,684,888 | 8/1972 | Knuflemann | 260/359 |

Primary Examiner—Harold A. Dixon
Attorney, Agent, or Firm—Dean E. Carlson; David S. Zachry; Louis M. Deckelmann

[57] ABSTRACT

A method of determining the pitch and eccentricity of the winding of a coil unit is provided. It specifically relates to nondestructively examining completely encased heating coils used to simulate the heat generated from fuel rods in reactor studies. The method comprises (1) the use of an x-ray transmission technique through the axial centerline of the coil unit after the winding of the coil unit has been completely encased, (2) the use of a radiation detection instrument to monitor the transmitted radiation, and (3) the use of recording instrumentation calibrated as a function of the distance between windings. A change in the pitch of the winding is detected by a general increase or decrease in the distance between recorded peaks of the transmitted radiation. Eccentricity is detected by a consistent variation in distance between peaks occuring in alternate pairs.

1 Claim, 5 Drawing Figures

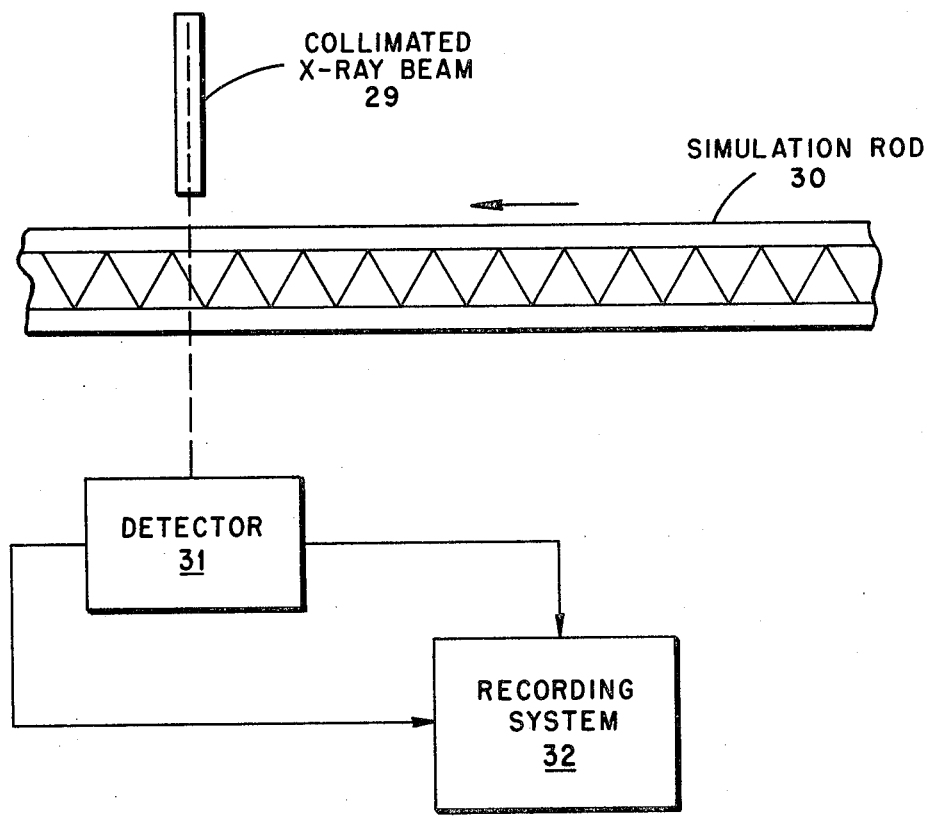

HIGH SPEED RADIATION SCANNING TECHNIQUE FOR SIMULTANEOUSLY DETERMINING THE PITCH AND ECCENTRICITY OF AN ENCASED OIL

BACKGROUND OF THE INVENTION

This invention was made in the course of, or under, a contract with the Energy Research and Development Administration.

In order to study the thermodynamic characteristic of nuclear fuel rods in nuclear reactors such as in the Liquid Metal Fast Breeder Reactor (LMFBR), Fast Flux Test Facility (FFTF), Gas Cooled Fast Reactor (GCFR), and Blow Down Heat Transfer (BDHT) programs, special resistance-heated pins have been designed to simulate actual thermal conditions. A heater pin typically consists of a metallic resistance coil or ribbon wound about an insulating core. The assembly is then completely encased in an insulating material and inserted in a metallic sleeve. It is crucial to the thermodynamic studies that the heater pins emit the designed heat, either constant or a programmed variable, thoughout the length of the pin; a variation in coil pitch or coil eccentricity causes uneven heat generation. It is therefore necessary to measure the pitch and monitor for eccentricities of the coil to assure proper assembly in the completed heater pin. Previously, the pitch has been monitored by manually measuring the distance between each coil on a series of radiographs of each heater pin; there was no quick method of determinimining coil eccentricity of the assembled heater pin.

Thus, there exists a need for an improved means and/or method for rapidly and accurately monitoring the pitch and eccentricity of a coil winding within a heater pin after fabrication. The present invention was conceived to meet this need in a manner to be described below.

SUMMARY OF THE INVENTION

It is the object of the present invention to provide a means and method of rapidly and accurately monitoring the pitch and eccentricity of a coil winding within a heater pin after fabrication.

The above object has been accomplished in the present invention by providing a method for determining any deviation in pitch or any eccentricity of an encased heating coil winding comprising the steps of longitudinally scanning encased coil by a collimated x-ray beam oriented perpendicular to the axis of the encased coil as the encased coil is moved across the beam, detecting the presence of the coil winding each time it intercepts the beam, and recording said interceptions to provide an indication of any deviation in pitch or any eccentricity of the coil windng along its length.

BRIEF DESCRIPTION OF THE DRAWINGS

FIG 1b illustrates a strip chart recording of the x-radiation transmission for the winding in FIG. 1a;

FIG. 2b illustrates a strip chart recording of the x-radiation transmission for the winding in FIG. 2a; and FIG. 3 is a schematic block diagram of a system for examining such coils.

DESCRIPTION OF THE PREFERRED EMBODIMENTS

A simplified block diagram of a detector system for examining completely encased heating coils for determining the pitch and eccentricity of such coils is illustrated in FIG. 3 of the drawings.

In FIG. 3, a collimated x-ray beam 29, which is oriented perpendicular to the axis of a heater rod 30, is used to longitudinally scan the rod as the rod is moved across the beam. The coil winding of the rod 30 is detected each time it intercepts the beam as a sharp decrease in transmitted radiation. A detector 31 monitoring the transmitted beam is connected to a strip chart recorder or computer 32 which records the exact location of each coil crossing and the corresponding radiation intensity.

Figure 1A:
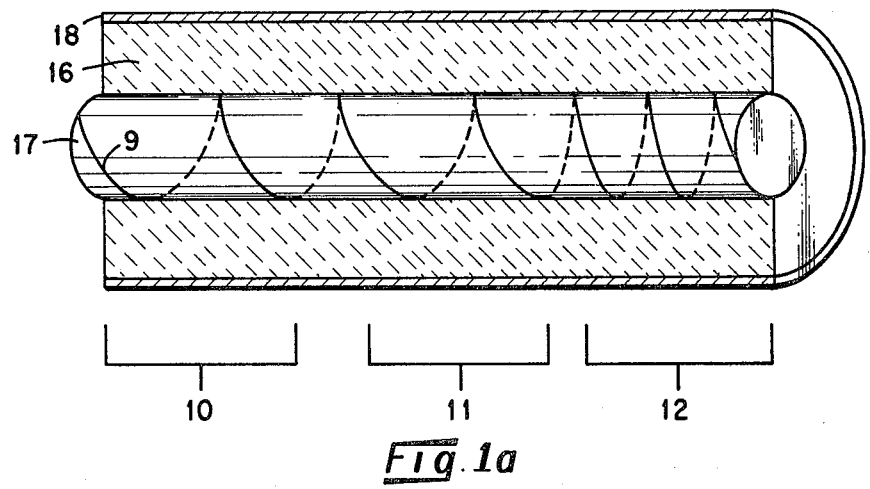
FIG. 1a illustrates a coil winding indicating varying pitch.
Figure 1B:
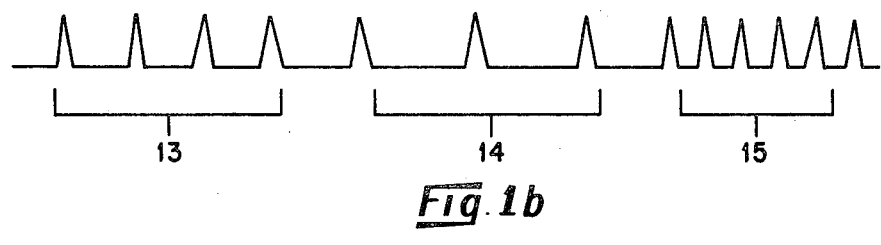

FIGS. 1a and 1b illustrate a change in pitch in a coil winding. FIG. 1a is a view of a heating coil 9 as it is wound on a core 17 of insulating material and encased in a housing of insulation 16, a protective metal sheath 18 encases the entire unit. The coil 9 is connected to an external power supply and control switch, not shown, in a conventional manner. The coil 9 has the desired pitch in section 10 of the heater rod. Section 11 depicts an increase in pitch, and section 12 depicts a decrease in pitch.

FIG. 1b illustrates a strip chart recording of the coil 9 as it moves along the center axis of FIG. 1a as detected by the system of FIG. 3. The strip chart recorder peaks in section 13 of FIG. 1b are evenly spaced. As the coil pitch increases, the distance between the recorder peaks reveals a corresponding increase as shown in section 14. Similarly, a decrease in pitch is denoted by a decrease in the distance between recorder peaks as shown in section 15.

Figure 2A:
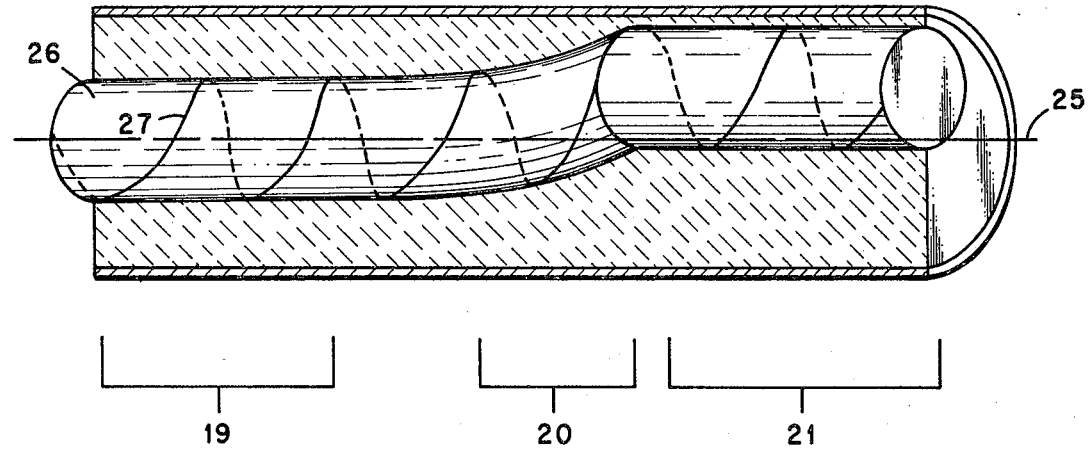
FIG. 2a is a drawing of a coil winding indicating winding eccentricites.
Figure 2B:
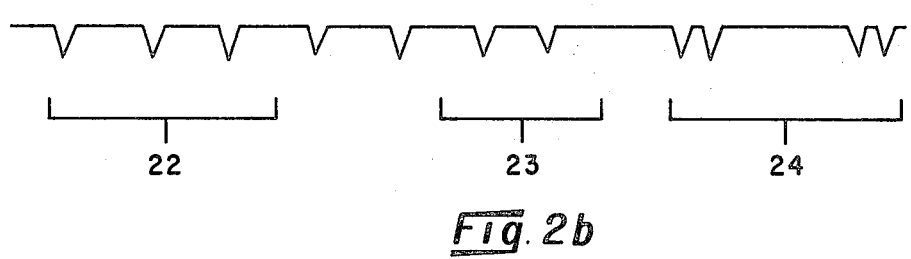

FIGS. 2a and 2b illustrates eccentricities in a coil winding. In FIG. 2a, the insulating core 26 on which the heating coil 27 is wound is misaligned in portions thereof causing the coil to be displaced from the axial line 25. Section 19 of the heater rod of FIG. 2a shows the core 26 properly aligned, while in sections 20 and 21 thereof, the core is not properly aligned such that there are eccentricities in the coil winding in the sections 20 and 21. It should be understood that the coil 27 of FIG. 2a is also connected to a suitable external power supply and control switch, not shown, in a conventional manner.

FIG. 2b illustrates a strip chart recording of the coil 27 as it moves along the center axis of FIG. 2a as detected by the system of FIG. 3. In sections 23 and 24 of FIG. 2b, the recorder peaks show a consistent variation. The peaks in sections 23 and 24 occur equally spaced in alternate pairs instead of successive equal spacings as in section 22.

From the above illustrations, it can be seen that a change in the pitch of a given coil winding is detected by a general increase or decrease in the distance between recorded peaks of the transmitted radiation, and that eccentricity is detected by a consistent variation in distance between recorded peaks occuring in alternate pairs.

In order to determine the above possible deviations from the desired orientation of the winding of an encased heating coil unit, the present invention comprises a method for determining such deviations comprising the steps of longitudinally scanning the encased coil unit by a collimated x-ray beam oriented perpendicular to the axis of the coil unit as the coil unit is moved across said beam, detecting the presence of the coil winding each time it intercepts the x-ray beam, and recording said interceptions to provide an indication of any deviation in pitch and/or any eccentricity of said coil winding along its length.

The above method is advantageous over the prior art method in that the pitch and eccentricity of a winding can be quickly and accurately monitored. The rate at which a tube length can be monitored is, of course, dependent on the scanning rate as well as the type of strip chart recorder or computer used in the operation. Present inspection rates utilizing the above method are in excess of five feet per minute. It can generally be stated that the above method far surpasses the previously used method in regard to its speed and accuracy.

This invention has been described by way of illustration rather than by limitation and it should be apparent that it is equally applicable in fields other than those described.

What is claimed is:

1. A method of determining any deviation in pitch or any eccentricity of the winding of an encased heating coil unit comprising the steps of longitudinally scanning said encased coil unit by a collimated x-ray beam oriented perpendicular to the axis of said coil unit as said coil unit is moved across said beam, detecting the presence of the coil winding each time it intercepts said beam, and recording said interceptions to provide an indication of any deviation in pitch and/or any eccentricity of said coil winding along its length.

* * * * *

UNITED STATES PATENT OFFICE
CERTIFICATE OF CORRECTION

Patent No. 3,999,067                Dated December 21, 1976

Inventor(s) Billy E. Foster

It is certified that error appears in the above-identified patent and that said Letters Patent are hereby corrected as shown below:

The final word in the title, "OIL" should be deleted and the word "COIL" inserted therefor.

*Signed and Sealed this*

*Seventeenth* Day of *May 1977*

[SEAL]

Attest:

RUTH C. MASON
*Attesting Officer*

C. MARSHALL DANN
*Commissioner of Patents and Trademarks*